United States Patent [19]

Webster et al.

[11] Patent Number: 5,057,634

[45] Date of Patent: Oct. 15, 1991

[54] MULTISTEP SYNTHESIS OF HEXAFLUOROPROPYLENE

[75] Inventors: James L. Webster, Parkersburg, W. Va.; Elrey L. McCann, Mendenhall, Pa.; Douglas W. Bruhnke, Landenberg, Pa.; Jan J. Lerou, Chadds Ford, Pa.; William H. Manogue, Newark, Del.; Leo E. Manzer, Wilmington, Del.; Steven H. Swearingen, Wilmington, Del.; Swiatoslaw Trofimenko, Wilmington, Del.; Cristobal Bonifaz, Conway, Mass.

[73] Assignee: E. I. Du Pont de Nemours and Company, Wilmington, Del.

[21] Appl. No.: 452,402

[22] Filed: Dec. 19, 1989

[51] Int. Cl.$^5$ .................. C07C 17/00; C07C 17/08
[52] U.S. Cl. .................... 570/157; 570/156; 570/165; 570/166; 570/168; 570/169
[58] Field of Search ............. 570/155, 156, 157, 168, 570/161, 175, 176

[56] References Cited

U.S. PATENT DOCUMENTS

| | | |
|---|---|---|
| 2,758,138 | 8/1956 | Nelson . |
| 2,900,423 | 8/1959 | Smith . |
| 2,970,176 | 10/1957 | Ten Eyck et al. . |
| 3,258,500 | 6/1966 | Swamer et al. . |
| 3,306,940 | 2/1967 | Halliwell . |
| 3,436,430 | 4/1969 | Hall . |
| 3,459,818 | 8/1969 | Ukihashi et al. . |
| 3,651,156 | 3/1972 | Scherer et al. . |
| 3,803,241 | 4/1974 | Stolkin et al. . |
| 3,865,885 | 2/1975 | Bruce . |
| 3,873,630 | 3/1975 | West . |
| 4,110,406 | 8/1978 | Anello et al. . |
| 4,814,522 | 3/1989 | Weigert . |

FOREIGN PATENT DOCUMENTS

| | | |
|---|---|---|
| 1070929 | 6/1967 | United Kingdom . |
| 1077932 | 8/1967 | United Kingdom . |

OTHER PUBLICATIONS

Sheppard & Sharts, Org. Fluor. Chem. 1969, pp. 74–81.
Hudlicky, Chem. of Org. Fluor. Compounds 1962, pp. 481–489.

*Primary Examiner*—Alan Siegel
*Attorney, Agent, or Firm*—Donald W. Huntley

[57] ABSTRACT

The present invention relates to multistep syntheses of hexafluoropropylene from acyclic three-carbon hydrocarbons or partially halogenated acyclic three-carbon hydrocarbons. In all these syntheses the first step is a vapor-phase chlorofluorination of the starting material to one or more saturated chlorofluorocarbons. Novel catalysts are also provided.

6 Claims, 3 Drawing Sheets

5,057,634

MULTISTEP SYNTHESIS OF HEXAFLUOROPROPYLENE

FIELD OF THE INVENTION

The present invention relates to multistep syntheses of hexafluoropropylene from acyclic three-carbon hydrocarbons or partially halogenated acyclic three-carbon hydrocarbons.

BACKGROUND OF THE INVENTION

Hexafluoropropylene has been prepared by the pyrolysis of tetrafluoroethylene. This process has several disadvantages. Tetrafluoroethylene, which is itself difficult to prepare and purify, is an explosive compound, which must be stored and handled with the greatest care. The pyrolysis of tetrafluoroethylene inevitably makes some perfluoroisobutylene as a by-product, and this compound is extremely toxic and is costly to remove and destroy.

Another preparative method for hexafluoropropylene is to make it simultaneously with tetrafluoroethylene by pyrolysis of $CHClF_2$. The product also contains the toxic by-product perfluoroisobutylene, and the process provides a particular mixture of the two products, which may be different from the ratio of products desired by the user. Both of the above synthetic methods are carried out at high temperatures, so it is necessary to make the equipment from rare and expensive metals. Patents describing these processes include U.S. Pat. Nos. 3,873,630, 2,970,176, 3,459,818, 2,758,138, and 3,306,940.

Vapor phase chlorofluorination of two-carbon hydrocarbons to make saturated halocarbons is known, but two-carbon hydrocarbons have only primary carbon-hydrogen bonds, while three-carbon hydrocarbons also have secondary carbon-hydrogen bonds, which have sharply different reactivity in reactions with halogens and halogen compounds.

Vapor phase chlorofluorination of higher hydrocarbons (containing three or more carbon atoms) or isopropyl fluoride is reported in U.S. Pat. Nos. 3,436,430, 3,865,885, and 4,110,406. The reactions described in these references give almost exclusively unsaturated products U.S Pat. No. 2,900,423 relates to the synthesis of hexafluoropropylene by hydrogenation of $CF_3$—$CFCl$—$CF_3$ over a catalyst. The patent gives no information about the washing step or the residual K in the catalyst. No information on catalyst life is presented, the longest run lasting only three hours.

Fluorination, (i.e., the reaction of a chlorinated hydrocarbon with HF to substitute F for Cl) is disclosed in U.S. Pat. No. 3,258,500. Transhalogenation (i.e., the exchange of one halogen atom in one compound for a halogen atom in another) is discussed in U.S. Pat. Nos. 3,651,156 and 4,814,522.

SUMMARY OF THE INVENTION

An object of the invention is to provide a process for the chlorofluorination of a feed containing at least one of the class consisting of propane, propylene, and a partially halogenated three-carbon acyclic hydrocarbon to make saturated perhalocarbon intermediates, followed by conversion to hexafluoropropylene.

A major aspect of the invention is a first step vapor phase process for the chlorofluorination of a feed containing at least one of the class consisting of propane, propylene, and a partially halogenated three-carbon acyclic hydrocarbon with $Cl_2$ and HF to make one or more of the saturated, fluorine-containing perhalocarbon intermediates A) $CF_3$—$CCl_2$—$CCl_3$,
B) $CF_3$—$CCl_2$—$CFCl_2$
C) $CF_3$—$CCl_2$—$CF_2Cl$,
D) $CF_3$—$CFCl$—$CF_2Cl$,
E) $CF_3$—$CCl_2$—$CF_3$, and
F) $CF_3$—$CFCl$—$CF_3$, This process is conducted at elevated temperature; e.g., between 100°–550° C., in the presence of a solid metal-containing salt or oxide which is stable at reaction conditions. Each of the above compounds A–F can be converted in an additional step or steps of the process of this invention into hexafluoropropylene. In some reaction sequences a mixture of these compounds can be used. It may be desirable to make or to use in subsequent steps only one or a few of the above perhalocarbons. It may also be desirable to recycle to the first chlorofluorination step those intermediates which contain H or contain double bonds or contain more Cl atoms than the halocarbon desired.

Selected catalysts are used to make the above saturated perhalocarbon intermediates. Catalysts and conditions can be selected to favor synthesis of any of the named perhalocarbons intermediates, with recycle of the underfluorinated intermediates. The synthesis of $CF_3$—$CCl_2$—$CF_3$ in particularly high yield is desirable. Novel catalysts have been made for the hydrodehalogenation of $CF_3$—$CFCl$—$CF_3$, and they give improved catalyst life.

The processes of this invention synthesize hexafluoropropylene without production of perfluorisobutylene.

DETAILED DESCRIPTION OF THE INVENTION DEFINITIONS

Figure 1:
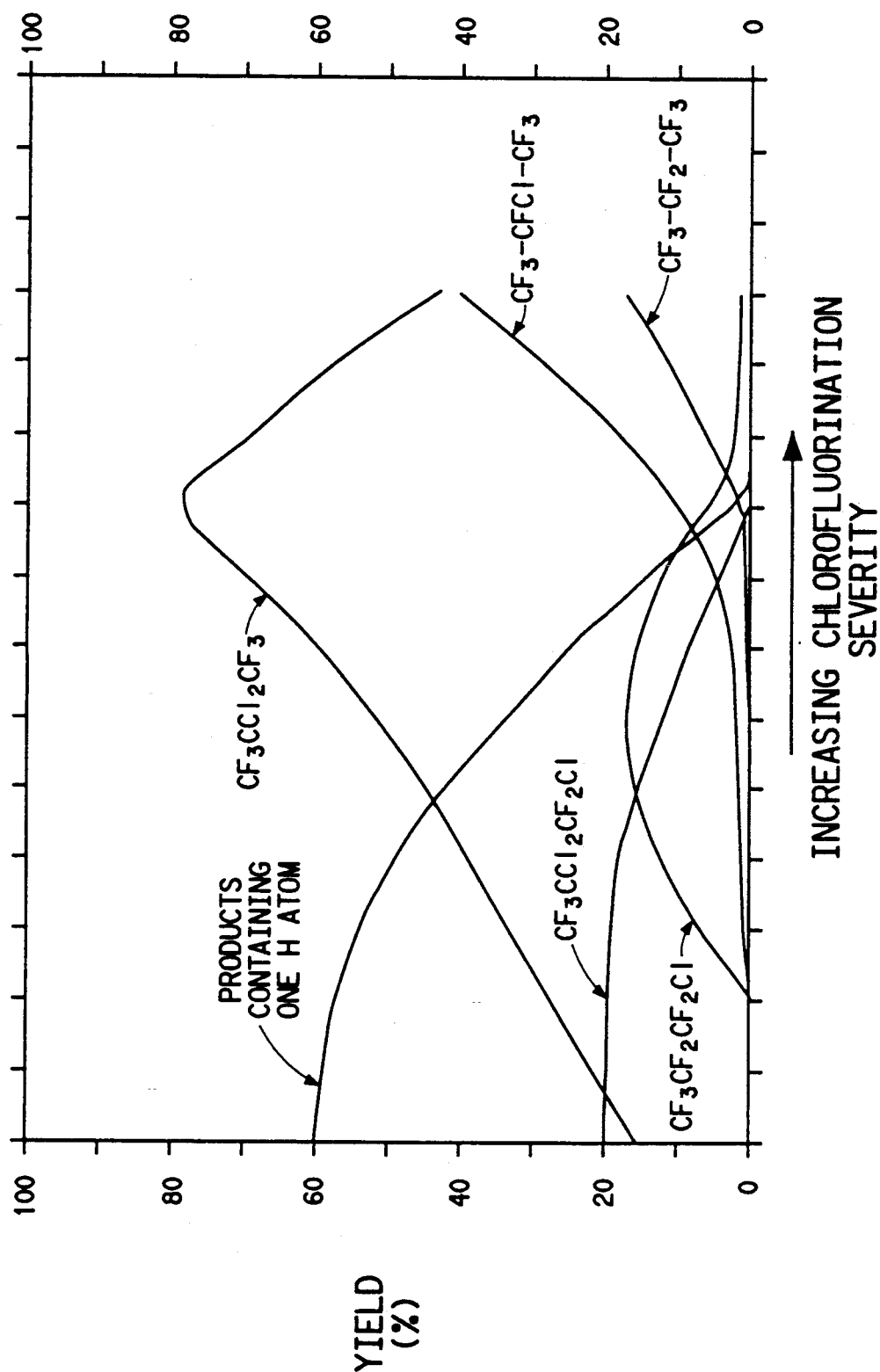

For the purpose of this disclosure:

Catalyst means a solid metal-containing catalytic salt or oxide as charged to the reactor. In many of the reactions described, the catalyst may undergo unknown changes in composition during pretreatment and reaction steps.

Contact time means the volume of catalyst charged to the reactor in ml, divided by the sum of all gas flow rates, in ml/sec, as measured at standard temperature and pressure.

Halogen means Cl and F.

Chlorofluorination means reaction of a feed containing at least one of the class consisting of propane, propylene, and a partially halogenated three-carbon acyclic hydrocarbon with a mixture of $Cl_2$ and HF.

Transhalogenation means the exchange of one halogen in one organic reactant for another halogen in the same or a different organic reactant.

Disproportionation is a special case in which transhalogenation occurs with only one reactant. In other words, it means the exchange of one halogen in the reactant for another halogen in another molecule of the same reactant.

In the following sequences of reactions, conventional procedures may be used for reactant and product isolation and, if desired, recycle. Especially useful techniques are fractional distillation or partial condensation. It is possible not only to have a separate recover system for each reaction, as is conventional, but in the case of chlorofluorination, fluorination with HF, dehalogenation with hydrogen, and transhalogenation, it is possible to combine the product streams for product isolation, recognizing that it is important for the sake of safety to remove elemental hydrogen carefully from the hydrogenation product mixture before combining the stream with other product mixtures that may contain elemental halogen.

Chlorine, HF, and HCl are separated by conventional methods. Thereafter, the lowest boiling material (after the removal of C-1 and C-2 byproducts) is $C_3F_8$, which is a useful by-product; the next is hexafluoropropylene, which is the final product desired; the next lowest boiling among saturated perhalocarbon intermediates is $CF_3$—$CFCl$—$CF_3$, which can be used in the last step of several sequences. Intermediates containing two or more chlorine atoms boil higher, and may be recycled with or without isolation.

The reaction sequences of the invention, including the final step resulting in hexafluoropropylene, are:

I. Sequence involving $CF_3$—$CFCl$—$CF_3$ intermediate
   a) Chlorofluorination of a feed containing at least one of the class consisting of propane, propylene, and a partially halogenated three-carbon acyclic hydrocarbon to $CF_3$—$CFCl$—$CF_3$. More lightly fluorinated by-products may optionally be recycled.
   b) Dehalogenation of $CF_3$—$CFCl$—$CF_3$ to hexafluoropropylene. In this reaction sequence, dehalogenation can be accomplished by reaction either with hydrogen or with a suitable metal.

II. Sequences involving $CF_3$—$CCl_2$—$CF_3$ intermediate:
IIA.
   a) Chlorofluorination of a feed containing at least one of the class consisting of propane, propylene, and a partially halogenated three-carbon acyclic hydrocarbon to $CF_3$—$CCl_2$—$CF_3$. Less highly fluorinated by-products such as $CF_3$—$CCl=CCl_2$, $CF_3$—$CCl_2$—$CF_2Cl$, and $CF_3$—$CCl_2$—$CFCl_2$ may be recycled to the chlorofluorination step (a) or are fed to the fluorination step (b), which is
   b) $CF_3$—$CCl_2$—$CF_3$ + HF → $CF_3$—$CFCl$—$CF_3$.
   c) Dehalogenation of $CF_3$—$CFCl$—$CF_3$ to hexafluoropropylene.

In this and the other reaction sequences, reaction with HF includes either high temperature vapor phase reaction or lower temperature reaction in the presence of a liquid phase catalyst such as $SbCl_5$/HF or $SbF_5$; the vapor phase process is preferred.

IIB.
   a) Chlorofluorination of a feed containing at least one of the class consisting of propane, propylene, and a halogen-containing three-carbon acyclic hydrocarbon to a mixture of $CF_3$—$CCl_2$—$CF_3$ and $CF_3$—$CFCl$—$CF_2Cl$. More lightly fluorinated by-products may optionally be recycled.
   b) Conversion of $C_3F_6Cl_2$ isomers to $CF_3$—$CFCl$—$CF_3$ either by transhalogenation or by reaction with HF. In the event of disproportionation, by-products can be recycled to step (a).
   c) Dehalogenation of $CF_3$—$CFCl$—$CF_3$ to hexafluoropropylene IIC.
   a) Chlorofluorination of a feed containing at least one of the class consisting of propane, propylene, and a partially halogenated three-carbon acyclic hydrocarbon to a mixture of $C_3F_6Cl_2$ and $C_3F_5Cl_3$ and $C_3F_4Cl_4$. More lightly fluorinated by-products may optionally be recycled.
   b) Reaction of all isomers produced with HF to give $CF_3$—$CFCl$—$CF_3$; recycling more lightly fluorinated by-products.
   c) Dehalogenation of $CF_3$—$CFCl$—$CF_3$ to hexafluoropropylene.

III. Sequence involving $CF_3$—$CCl_2$—$CF_2Cl$ intermediate:
   a) Chlorofluorination of a feed containing at least one of the class consisting of propane, propylene, and a partially halogenated three-carbon acyclic hydrocarbon to $CF_3$—$CCl_2$—$CF_2Cl$. More lightly fluorinated by-products may optionally be either recycled or fed to fluorination step (b).
   b) $CF_3$—$CCl_2$—$CF_2Cl$ + HF → $CF_3$—$CFCl$—$CF_3$ and $CF_3$—$CCl_2$—$CF_3$, recycling the $CF_3$—$CCl_2$—$CF_3$ formed to step (b).
   c) Dehalogenation of $CF_3$—$CFCl$—$CF_3$ to hexafluoropropylene.

IV. Sequence involving $CF_3$—$CCl_2$—$CFCl_2$ and $CF_3$—$CCl_2$—$CCl_3$ intermediates:
   a) Chlorofluorination of a feed containing at least one of the class consisting of propane, propylene, and a partially halogenated three-carbon acyclic hydrocarbon to $CF_3$—$CCl_2$—$CFCl_2$ and/or $CF_3$—$CCl_2$—$CCl_3$.
   b) $CF_3$—$CCl_2$—$CFCl_2$ and/or $CF_3$—$CCl_2$—$CCl_3$ + HF → $CF_3$—$CFCl$—$CF_3$.
   c) Dehalogenation of $CF_3$—$CFCl$—$CF_3$ to hexafluoropropylene.

CHLOROFLUORINATION

The catalysts which are effective for the chlorofluorination of a feed containing at least one of the class consisting of propane, propylene, and a partially halogenated three-carbon acyclic hydrocarbon include compounds of the metallic elements. In use they may be in the form of their fluorides, oxyfluorides, chlorides, oxychlorides or oxides, but as charged to the reactor they may be in the form of any compounds convertible to the above compounds under reaction conditions, such as pseudohalides and acid salts. They may be used either alone or in combination and in the presence or absence of a support such as, but not limited to, elemental carbon. Some minerals such as ceria and didymia contain mixtures of rare earths such as La, Sm, Nd, and Pr, and the salts of these minerals may be more practical to use than those of the pure elements.

Preferred catalysts for the synthesis of $C_3F_7Cl$ are $Cr_2O_3$, $Cr_2O_3$ on alumina, and mixed oxides of Cr and Mn. Preferred catalysts for the synthesis of $C_3F_6Cl_2$ are supported salts of at least one of Co, Nd, Fe, Cr, Rh, Ce, Y, Ni, La; a compound of Al; and $La_{0.8}Ce_{0.2}CrO_3$. Preferred catalysts for the synthesis of mixtures of $C_3F_6Cl_2$, $C_3F_5Cl_3$, $C_3F_4Cl_4$, and $C_3F_3Cl_5$ are supported catalysts containing at least one of Zn, Cu, Co, La, Pr, Cr, Y, Rh, Nd, Ce, Fe, Sm, and Sn. Acceptable results can be obtained with other metal-containing catalysts, provided the temperature, contact time, and other reaction conditions are suitably selected.

In the catalytic chlorofluorination of a feed containing at least one of the class consisting of propane, propylene, and a partially halogenated three-carbon acyclic hydrocarbon according to this invention, a temperature may be employed of between 100° C. and 550° C. However, the preferred temperature is 200° C. to 500° C. The most preferred temperature is 300° C. to 450° C. The temperature used depends on the contact time chosen, the catalyst used, and the time the catalyst has been on stream.

In the chlorofluorination of propane/propylene the concentration of chlorine in relationship to propane/propylene may vary over a fairly broad range. Illustratively, mole ratios of chlorine to propane may be from 8 to 25, with the preferred range being 9 to 20 and the most preferred range being 10 to 14. Mole ratios of chlorine to propylene may be from 7 to 25, with a preferred range being 7 to 20 and the most preferred range being 8 to 16.

In the chlorofluorination of propane/propylene the concentration of hydrogen fluoride in relationship to propane/propylene may vary over a fairly broad range. Illustratively, mole ratios of hydrogen fluoride to propane/propylene may be from 3 to 110, with a preferred range of 20 to 60, and most preferred range of 30 to 50.

The ratio of HF to chlorine can be varied over the range of 1-7. It is preferable to use higher HF:chlorine ratios, such as 2-7, to make highly fluorinated products, such as $CF_3$—$CFCl$—$CF_3$.

The above discussion of reactant ratios is based on the assumption that partially halogenated products are not being recycled. The large amounts of HF and $Cl_2$ are preferred because the chlorofluorination reaction is so exothermic that it is desirable to operate adiabatically, with large amounts of cooled recycle feed absorbing the heat given off by the chlorofluorination reaction.

In practice, it is convenient to recycle halocarbons that are not fluorinated to the desired degree, so that they will be converted to desired products. Alternatively, in addition, inert gases may be added and recycled to act as heat sink in an approximately adiabatic reactor. When recyclable intermediates or inert gases are recycled to the chlorofluorination step, the weight of HF and $Cl_2$ in excess of the stoichiometric requirement can be reduced. More detail about recycling of intermediates can be found in the discussion below of reaction sequence I, step (a).

In addition to propane, propylene, recycled intermediates, and mixtures thereof, it is also possible to feed to the chlorofluorination reaction a partially halogenated three-carbon acyclic compound. As one example, 1,2-dichloropropane is readily available and can be used as the starting material, alone or with other feed materials specified above.

The reaction pressure is not critical. Preferably it may be between 1 and 40 atmospheres. About 20 atmospheres is preferred to allow easy separation of HCl from the halocarbons without requiring compression.

The yield of desired products will be determined to a large extent by the temperature and contact time of the reactant materials with the catalyst. Contact times of the order of 300 seconds or less are suitable. Preferred contact times are 0.01 to 100 seconds. Most preferred contact times are 0.05 to 15 seconds.

When catalysts are relatively inactive or when mild chlorofluorination conditions of temperature, contact time, and reactant ratios are used, the products obtained still contain hydrogen, and are often unsaturated. Somewhat more strenuous conditions or more active catalysts give unsaturated products in which all hydrogen atoms have been replaced with halogen. The still more strenuous conditions and/or more active catalysts employed in the process of the present invention give saturated halocarbons which are rich in Cl. The most strenuous conditions or active catalysts give highly fluorinated propanes such as $CF_3$—$CFCl$—$CF_3$. In all cases, recycle of under-chlorofluorinated three-carbon intermediates results in further chlorofluorination and eventually in highly fluorinated halopropanes. The preferred temperature, contact time, and reactant ratios depend on the catalyst in use, how long it has been on stream, and the chlorofluoropropanes desired to be produced.

Figure 2:
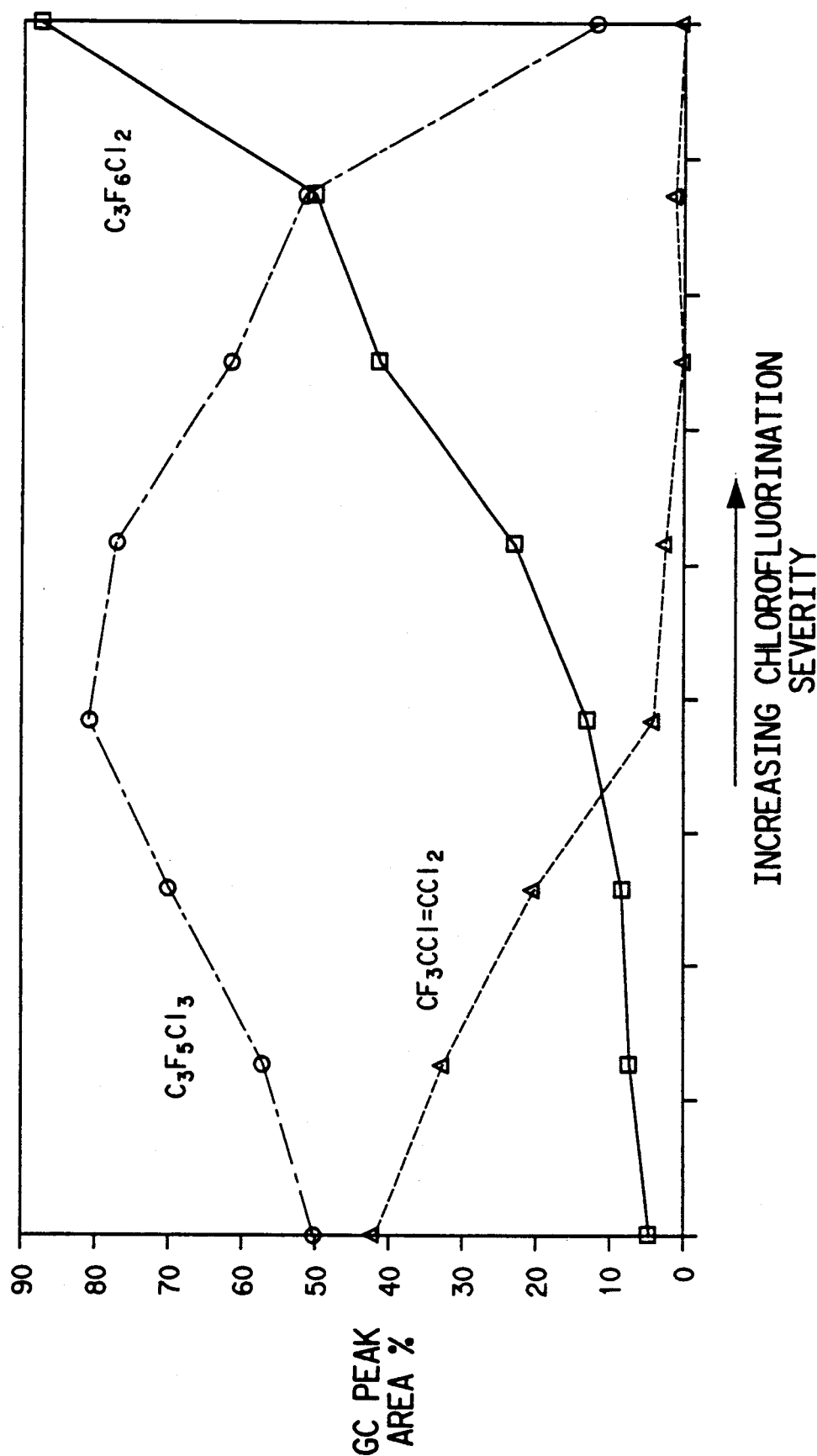
Figure 3:
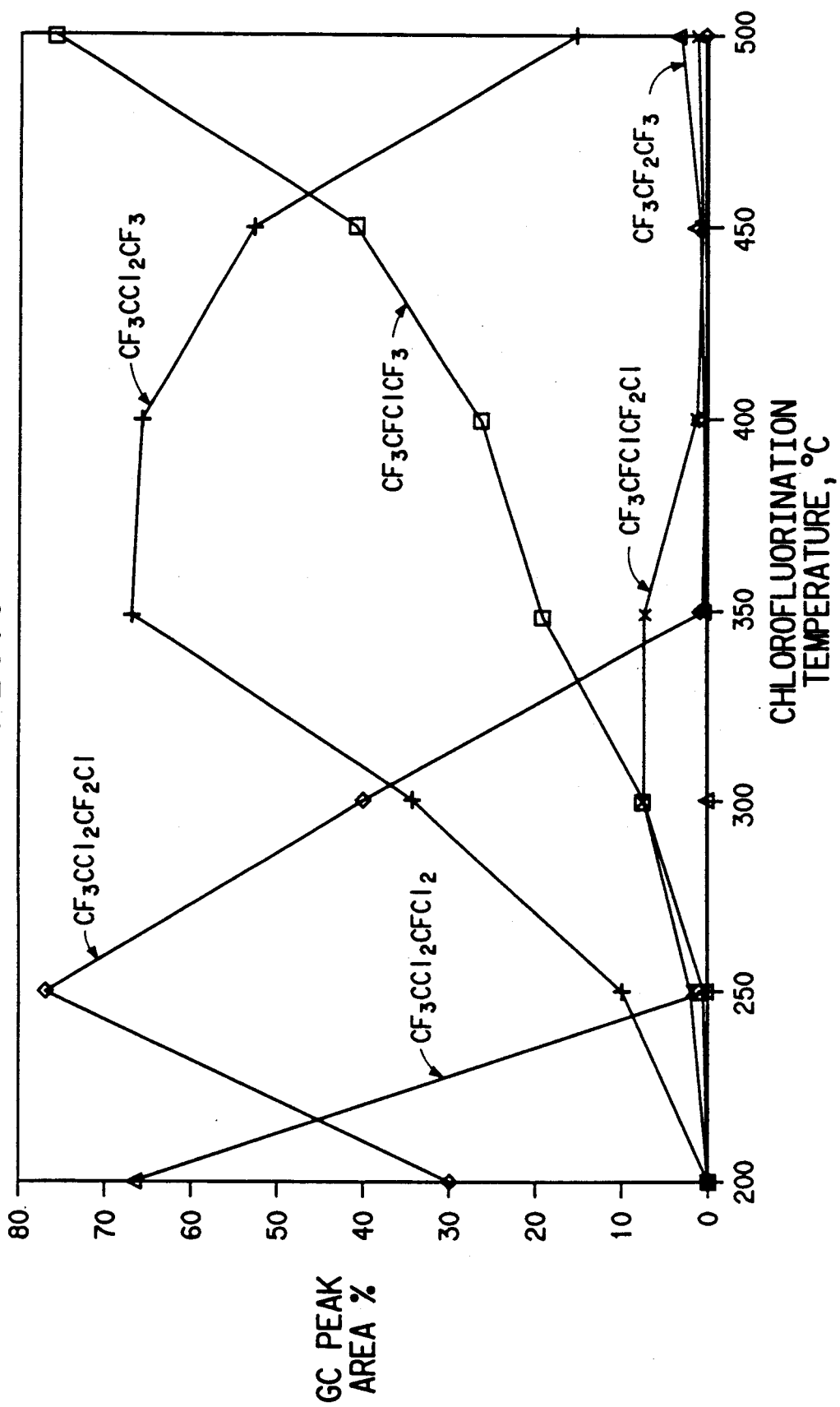

FIG. 1 illustrates schematically how the conversion to the various chlorofluoropropanes referred to in the previous paragraph changes with increasing severity of conditions when propylene is chlorofluorinated over $CrO_x$ on $Cr_2O_3$; the severity of conditions was varied by changing contact time or temperature. FIG. 2 also illustrates this point, using a different catalyst, $CrCl_3$ on carbon. The abscissa represents increased chlorofluorination severity, as achieved by varying the HF:propylene ratio from 17 to 30, varying the temperature from 400° to 440° C., and varying the contact time from 2 to 20 seconds. The first few points are at HF:propylene=17° and 400° C., varying contact time from 2 to 15 seconds. The last few points are at HF:propylene=30 and 9 seconds contact time, varying the temperature from 400° to 440° C. FIG. 3 also illustrates this point. In this series of experiments, $CF_3$—$CCl$=$CCl_2$ was chlorofluorinated over a $Cr_2O_3$ catalyst at a contact time of 16 seconds and at a series of temperatures. This figure shows quite clearly the sequence in which various products are formed and the tunability of this novel chemistry to provide a desired product.

While many of the experiments reported used propylene as the feed hydrocarbon, propane can be used with similar effectiveness. Examples 101-105 illustrate this point, using the same catalyst, chlorine:propane ratio, and HF:propane ratio, but different contact times; all these examples gave at least 97% total yield to useful products.

GENERAL PROCEDURE FOR CHLOROFLUORINATION

The reactor was an Inconel ® tube with an outside diameter of 0.5 inch (1.27 cm), shaped like a squared U. It was charged with the desired amount of catalyst, usually 20 ml, and purged with nitrogen. The reactor temperature was increased via a heated fluidized sand bath to 450° C. The nitrogen flow was maintained through the reactor during the heating period. When a temperature of about 450° C. was achieved, the HF flow was initiated and the nitrogen flow was discontinued. The temperature was then adjusted to the desired value. The HF flow was decreased to the desired value followed by initiating the chlorine and propane (or propylene) flow at the desired value. Alternatively, after heating the catalyst at 450° C., the temperature was lowered to 150° C. A $N_2$/HF flow was started over the catalyst and the temperature slowly raised to the reaction temperature.

GENERAL PROCEDURE FOR PRODUCT ANALYSIS

Product analysis was achieved by gas chromatography using a 3 m column from Supelco packed with 5% Krytox ® fluorinated oil supported on Carbopack ® B graphite carbon black. Sample injection was accomplished by an on-line sample valve. The analysis was done at 70° C. for 8 minutes followed by temperature programming at 8 degrees per minute up to 200° C. and held at 200° C. for an additional 16 minutes. Product analyses are reported as relative area %.

GENERAL PROCEDURE FOR PREPARING CATALYST MCl$_x$C (C herein represents carbon, M represents metal, and x represents the valence of M)

The desired amount of metal chloride was dissolved in 35 to 75 ml of water and the entire solution poured over 40 cc of commercial carbon granules (Girdler 411, 0.32 cm pellets). The resulting mixture was allowed to stand at room temperature for one hour and was then placed in a vacuum oven at 110° C. for 16 to 24 hours to remove the water. The catalyst was then pretreated by heating in an atmosphere of nitrogen gas at 450° C. followed by heating in HF at 450° C. prior to its use as a chlorofluorination catalyst.

CATALYST PREPARATION

The following catalysts were prepared by the general procedure for MCl$_x$/C:

| Catalyst | Starting Material |
| --- | --- |
| FeCl$_3$/C | 39.7 g FeCl$_3$.6H$_2$O/35 cc H$_2$O |
| ZnCl$_2$/C | 20.44 g ZnCl$_2$/75 cc H$_2$O |
| RhCl$_3$/C | 2.0 g RhCl$_3$/75 cc H$_2$O |
| LaCl$_3$/C | 62.43 g LaCl$_3$.7H$_2$O/75 cc H$_2$O |
| CrCl$_3$/C(.01X) | 0.29 g CrCl$_3$.6H$_2$O/60 cc H$_2$O |
| CrCl$_3$/C(1X) | 39.17 g CrCl$_3$.6H$_2$O/60 cc H$_2$O |
| NdCl$_3$/C | 57.39 g NdCl$_3$.6H$_2$O/75 cc H$_2$O |
| CeCl$_3$/C | 57.41 g CeCl$_3$.8H$_2$O/75 cc H$_2$O |
| YCl$_3$/C | 48.54 g YCl$_3$.6H$_2$O/75 cc H$_2$O |
| PrCl$_3$/C | 56.86 g PrCl$_3$.6H$_2$O/75 cc H$_2$O |
| SmCl$_3$/C | 58.37 g SmCl$_3$.2O/75 cc H$_2$O |
| (ZnCl$_2$ + CoCl$_2$)/C | 30 g ZnCl$_2$/35 g CoCl$_2$.6H$_2$O/80 cc H$_2$O |
| (CuCl$_2$ + CoCl$_2$)/C | 2.56 g CuCl$_2$.2H$_2$O/35.0 g CoCl$_2$.6H$_2$O/75 cc H$_2$O |
| (KCl + CoCl$_2$)/C | 1.12 g KCl/35 g CoCl$_2$.6H$_2$O/75 cc H$_2$O |
| (LaCl$_3$ + CoCl$_2$)/C | 5.57 g LaCl$_3$.7H$_2$O/35 g CoCl$_2$.6H$_2$O/75 cc H$_2$O |

The CrCl$_3$/C catalyst was 29% CrCl$_3$ on carbon.

PREPARATION OF CoO/Cr$_2$O$_3$

Cr$_2$O$_3$, 100 g, was slurried in a solution of 4.94 g of cobalt nitrate in 500 ml of distilled water for 30 minutes. The water was then removed from the solution via a rotary evaporator and the crude catalyst was dried in a vacuum oven and then heated at 450° C. for one hour.

PREPARATION OF NiO/Cr$_2$O$_3$

Cr$_2$O$_3$, 100 g, was slurried in a solution of 5.0 g of nickel nitrate in 500 ml of distilled water for 30 minutes. The water was then removed from the solution via a rotary evaporator and the crude catalyst was dried in a vacuum oven and then heated at 450° C. for one hour.

PREPARATION OF Cr-oxide ON ALUMINA

CrCl$_3$.6H$_2$O, 134 g, was dissolved in 1000 cc H$_2$O. To this solution was added 45 g of a low alkali metal content Al$_2$O$_3$. The slurry was stirred and heated to 90° C. The pH of the hot solution was adjusted to 9 with concentrated ammonium hydroxide. The solution was stirred for one hour at 90° C. and then allowed to cool to room temperature. The crude solid was filtered, washed five times with 100 cc of H$_2$O and dried in a vacuum oven at 110° C. The catalyst was mixed with 1-5 weight % "Sterotex" powdered lubricant (registered trademark of Capital City Products Co, Columbus, Ohio, division of Stokely-Van Camp, for its edible hydrogenated vegetable oil) to give ⅛" diameter ×3/16" long cylindrical pellets from a Stokes tablet machine.

PREPARATION OF Cr-oxide/AlF$_3$

CrCl$_3$.6H$_2$O, 134 g, was dissolved in 1000 cc H$_2$O. To this solution was added 45 g of AlF$_3$. The slurry was stirred and heated to 90° C. The pH of the hot solution was adjusted to 9 with concentrated ammonium hydroxide. The solution was stirred for one hour at 90° C. and then allowed to cool to room temperature. The crude solid was filtered, washed five times with 100 cc of H$_2$O and dried in the vacuum oven at b 110° C. The catalyst was mixed with 1-5 weight % "Sterotex" powdered lubricant to give ⅛" diameter ×3/16" long cylindrical pellets from a Stokes tablet machine.

PREPARATION OF RhCl$_3$/Cr$_2$O$_3$

Cr$_2$O$_3$, 100 g, was slurried in a solution of 2.6 g of RhCl$_3$ in 500 ml of distilled water for 30 minutes. The water was then removed from the solution via a rotary evaporator and the crude catalyst was dried in a vacuum oven and then fired at 400° C. for one hour.

PREPARATION OF Cr$_{0.5}$Mn$_{0.5}$O$_2$

Cr(NO$_3$)$_3$.9H$_2$O, 400.15 g, and 287.06 g of Mn(NO$_3$)$_2$.6H$_2$O was dissolved in 1000 cc H$_2$O. The pH of the solution was adjusted to 9 with concentrated ammonium hydroxide. The crude solid was collected by filtration and dried in the vacuum oven and fired overnight at 500° C. The catalyst was mixed with 1-5 weight % "Sterotex" powdered lubricant to give ⅛" diameter ×3/16" long cylindrical pellets from a Stokes tablet machine.

PREPARATION OF La$_{0.8}$Ce$_{0.2}$CrO$_3$

La(NO$_3$)$_3$.6H$_2$O, 346.4 g, 86.8 g of Ce(NO$_3$)$_3$.6H$_2$O and 400.15 g of Cr(NO$_3$)$_3$.9H$_2$O were dissolved in 1000 cc H$_2$O. The pH of the solution was adjusted to 9 with concentrated ammonium hydroxide. The crude solid was collected by filtration, washed with water and dried in the vacuum oven. The catalyst was fired at 600° C. for four days with daily grinding and mixing. The catalyst was mixed with 1-5 weight % "Sterotex" powdered lubricant to give ⅛" diameter ×3/16" long cylindrical pellets from a Stokes tablet machine.

PREPARATION OF Zr$_{0.5}$Cr$_{0.5}$O$_{1.5-2.0}$

ZrO(NO$_3$).xH$_2$O, 100 g, and 159 g of Cr(NO$_3$)$_3$.9H$_2$O was dissolved in 2750 cc of H$_2$O. The pH of the solution was adjusted to 9 with concentrated ammonium hydroxide while vigorously stirring the solution. The crude solid was collected by filtration, washed with water and dried in the vacuum oven. The catalyst was fired at 500° C. overnight. The catalyst was mixed with 1-5 weight % "Sterotex" powdered lubricant to give ⅛" diameter ×3/16" long cylindrical pellets from a Stokes tablet machine.

PREPARATION OF La$_{0.7}$Sr$_{0.3}$CrO$_{0.7}$F$_{0.6}$

La(NO$_3$)$_3$.6H$_2$O, 303.1 g, 400.2 g of Cr(NO$_3$)$_3$.9H$_2$O was dissolved in 1000 cc of H$_2$O. The pH of the solution was adjusted to 9 with concentrated ammonium hydroxide. SrF$_2$, 37.7 g, was added and the slurry was stirred for 30 minutes. The crude solid was collected by filtration, washed with 500 cc of $H_2O$ and dried in a vacuum oven. The catalyst was fired 4 days at 600° C. with daily grinding and mixing. The catalyst was mixed with 1-5 weight % "Sterotex" powdered lubricant to give ⅛" diameter×3/16" long cylindrical pellets from a Stokes tablet machine.

PREPARATION OF $CrO_x$ ON $Cr_2O_3$

In 2000 ml of water was dissolved 160 g $CrO_3$. Eight portions of 10 ml ethanol were added at 5-minute intervals, with stirring. The mixture was stirred for 4 hours, and then 80 ml more ethanol was added with stirring. The mixture was refluxed overnight with stirring. The entire mixture was evaporated to dryness in a rotary vacuum drier, allowing the remaining dissolved solids to deposit on the chromia gel. Then drying was completed in a vacuum oven at 110° C. Pellets 0.125" (3.18 mm) in diameter were formed after the addition of 1% "Sterotex" powdered lubricant.

DEHYDRATION OF $Cr_2O_3$ CATALYSTS

When hydrous chromium oxide is used in making a catalyst, that catalyst is preferably heated to 450° C. for about one hour with a flow of a gaseous diluent such as nitrogen, to dehydrate the hydrous chromium oxide before the catalyst is used.

CHLOROFLUORINATION EXAMPLES

In all of the Examples herein:
Yield, as reported in the examples, is calculated from peak areas obtained in gas chromatographic analysis. This is a common technique in product identification, even though various compounds have somewhat different response factors.

Conversion of hydrocarbon in all chlorofluorination reactions is complete. Conversion to a particular product in the examples is calculated from peak areas obtained in gas chromatographic analysis.

Temperature in a tubular reactor of less than about 1 cm in diameter is measured with a thermocouple in the heat transfer medium outside the tube. Temperature in a tubular reactor of more than about 1 cm diameter is measured with a thermocouple in an internal well. In large scale reactors, there are several thermocouples in the well so that the temperature profile can be observed.

The conditions and results of propylene chlorofluorination experiments directed toward saturated halocarbons are recorded in Table I (Examples 1 to 22), in which Ct means contact time in seconds, and other abbreviations are defined. Examples which are preferred for making $CF_3$—$CCl_2$—$CF_2Cl$ are 6 and 21. Examples which are preferred for making $CF_3$—$CCl_2$—$CF_3$ as the major product are Examples 1 to 6. Example 9 makes a mixture of $CF_3$—$CCl_2$—$CF_3$ and $CF_3$—$CFCl$—$CF_2Cl$.

Note that the footnote to Table I explains that the remainder of the products consists of materials which are underhalogenated and can be recycled. This means that the yield to the most highly fluorinated product mentioned approaches 100%, provided recyclable intermediates are recycled in equally high yield.

The metal salt or oxide catalysts employed in the preferred process of this invention are considerably more active than carbon pellets alone. This is illustrated in Table II, in which the temperatures, contact times, and ratios of reactants are similar. Note that considerably larger quantities of saturated perhalocarbons are made when the promoted catalysts are used.

To make $CF_3$—$CFCl$—$CF_3$ and recyclable intermediates, propylene was chlorofluorinated over CrOx on $Cr_2O_3$ as shown in FIG. 1.

Examples of the chlorofluorination of propane are summarized by Examples 24 to 28 in Table III, showing that $CF_3CCl_2CF_3$ was made in conversions of up to 81%, with yields to this product plus recyclable intermediates of 85-88%.

SYNTHESES OF HEXAFLUOROPROPYLENE

I. Sequence of Reactions Based on $CF_3$—$CFCl$—$CF_3$

Sequence I is attractive because it requires only two steps, with resultant process simplification and reduction in plant investment and operating cost.

a) Chlorofluorination of propane and/or propylene and/or partially halogenated three-carbon acyclic hydrocarbon to $CF_3$—$CFCl$—$CF_3$, optionally recycling all more lightly fluorinated intermediates (see the section on Chlorofluorination Examples, and particularly see the Examples of Sequence I.

b) Dehalogenation of $CF_3$—$CFCl$—$CF_3$ to hexafluoropropylene. In this reaction sequence, dehalogenation can be accomplished by reaction with hydrogen or a suitable metal.

(i) Hydrogenation. While any hydrogenation catalyst could be used, the most active catalysts, such as Pt and Pd, are poor selections because, in addition to the desired products, they lead to the addition of hydrogen across any double bond present or to the substitution of hydrogen for chlorine, thus reducing the yield of desired products and requiring recycle. These effects are not desirable, but do not substantially reduce the overall yield to hexafluoropropylene, because the hydrogen-containing by-products can be recycled to the chlorofluorination step. Catalysts containing excessive amounts of Ni may give this somewhat undesirable result.

Catalysts which are preferred include, as charged to the reactor, common hydrogenation catalysts such as Cu, Ni, Cr, or combinations thereof, optionally promoted with compounds of Mo, V, W, Ag, Fe, K, Ba, or combinations thereof. It is not critical whether the catalysts are supported or not, but some of the better catalysts include unsupported copper chromite. However, supports which are unreactive to halocarbons, HF, and oxygen at hydrogenation temperatures and up to 100° higher such as metal fluorides, alumina, and titania, may be used. Particularly useful are supports of fluorides of metals of Group II of the Mendeleeff periodic table, particularly Ca. A preferred catalyst is made of equimolar quantities of Cu, Ni, and $Cr_2O_3$ on $CaF_2$.

An especially preferred catalyst contains 1.0 mole CuO, 0.2-1 mole NiO, 1-1.2 moles $Cr_2O_3$ on 1.3-2.7 moles of $CaF_2$, promoted with 1-20 weight %, based on the total catalyst, of an alkali metal selected from K, Cs, and Rb, preferably K. When K is the promoter, the preferred amount is 2-15 weight % of the total catalyst, but the method of adding the K is not critical. For example, it may be added as a salt or base.

This catalyst is not only useful for the reaction $CF_3$—$CFCl$—$CF_3+H_2 \rightarrow CF_3CF=CF_2$, but also for corresponding hydrodehalogenations $CFCl_2$—$CF_2Cl + H_2 \rightarrow CFCl=CF_2$ and $CF_2Cl$—$CF_2Cl + H_2 \rightarrow CF_2=CF_2$.

The catalyst is prepared by coprecipitating, from an aqueous medium, salts of copper, nickel and chromium with and preferably on calcium fluoride; washing, heating, filtering and drying the precipitate; depositing an alkali metal salt on the precipitate; and calcining the precipitate to convert the copper, nickel and chromium to the respective oxides. Copper, nickel and chromium salts suitable for use herein include the chlorides, fluorides and nitrates, with the nitrates being especially preferred.

The catalyst may be granulated, pressed into pellets, or shaped into other desirable forms. The catalyst may contain a binder to help ensure the physical integrity of the catalyst during granulating or shaping the catalyst into the desired form. Suitable binders include carbon and graphite, with carbon being preferred. When a binder is added to the catalyst, it normally comprises about 0.1 to 5 weight percent of the weight of the catalyst.

Another group of catalysts which showed good lifetime in the hydrodehalogenation of $CF_3$—$CFCl$—$CF_3$, $CF_2Cl$—$CF_2Cl$, or $CFCl_2$—$CF_2Cl$ is 1.0 $CuO$/0.2–1 $NiO$/1–2 $Cr_2O_3$/0.4–1 $MoO_3$/0.8–4 $CaF_2$, optionally promoted with at least one compound from the group consisting of $MgF_2$, $MnF_2$, and $BaF_2$ or with a trace of Pd or $WO_3$. Two of these hydrodehalogenation runs were shut down after 153 and $_{361}$ hours, respectively, while still giving good results.

After it is charged to the reactor, the hydrogenation catalyst is reduced with hydrogen at or somewhat above the desired reaction temperature before the chlorofluorocarbon feed is started.

After use in the hydrogenation reaction for a period of time, the activity of the catalyst may decrease. When this occurs, the catalyst activity can be regenerated by stopping the flow of halocarbon, flushing the bed with a gas such as hydrogen, air, or oxygen, at a temperature near or up to 100° higher than the hydrogenation temperature for at least several minutes. (A temperature higher than the hydrogenation temperature is normally used, but a lower temperature can be used with hydrogen.) After the flushing step, the reactor temperature is readjusted to the hydrogenation temperature before resuming the hydrogenation reaction. While the inventors do not wish to be bound by any hypothesis, it is believed possible that catalyst activity deteriorates when the halocarbon feed deposits a small amount of polymer on the catalyst. Heating to a higher temperature in the presence of a flowing gas may pyrolyze the polymer to volatile fragments, which are swept away by the gas. The nature of the gas is not critical, but hydrogen is preferred.

A suitable temperature for the hydrogenation step is 250°–550° C., preferably 350°–475°, and most preferably 400°–450°. A suitable contact time is 0.1–120 seconds. A preferred contact time is 0.3–60 seconds, and the most preferred contact time is 0.5–15 seconds.

Suitable pressure in step (b) is 0–100 atmospheres gauge. Preferred is 0–50 atmospheres, and most preferred is 2–30 atmospheres.

As those skilled in the art appreciate, there is a relationship between catalyst activity, temperature, pressure, and contact time such that more active catalyst and higher pressure permit operation at lower temperature and shorter contact time.

(ii) Dehalogenation with a metal. The elements of $Cl_2$ or $ClF$ can be removed from a halocarbon using a metal such as Zn, Mg, Cu, Fe, or Ni or a combination of such metals. It is preferable to use Zn. It is also preferable to use a polar organic solvent for this reaction, such as an alcohol, ether, dioxane, anhydride, or nitrile. The temperature may be 25°–200° C., preferably 70°–200° C., and the time of reaction, which depends on the reagent and the temperature, can be determined by routine experimentation.

EXAMPLES OF SEQUENCE I

Step Ia) Chlorofluorination

In this work the catalyst charged was chromium oxide trihydrate, and dehydration of the catalyst was conducted at 400° C. with a flow of HF.

Pressure reactions were carried out in a 1 inch by 7 foot ($_{2.54}$ cm by 2.1 m) Inconel ® tubular reactor with excess HF to absorb most of the evolved heat. It was possible to maintain catalytic activity over a period of four weeks, operating during the day shift only, and at this time the reactor was shut down voluntarily.

EXAMPLE 29

Feed rates in mols/hour were 44 HF, $_{22}$ $Cl_2$, and 1 propylene. Operation was at 420° C. at 115 pounds/square inch absolute (790 kPa). The conversions to various products were:

$C_3F_7Cl$: 30
$C_3F_6Cl_2$: 52
$C_3F_5Cl_3$: 8
$C_3F_7H$: 5
$C_3F_6ClH$: 5
$C_3F_5Cl_2H$: 0.1
$C_3F_8$: 0.9
$C_2F_5Cl$: 0.3

EXAMPLE 30

The conditions were the same as in the previous example except the temperature was 390° C. The conversions to various products were:

$C_3F_7Cl$: 18
$C_3F_6Cl_2$: 45
$C_3F_5Cl_3$: 12
$C_3F_7H$: 7
$C_3F_6ClH$: 14
$C_3F_5Cl_2H$: 3
$C_3F_6H_2$: 0.1
$C_3F_8$: 0.1
$C_2F_5Cl$: 0.5

In these examples all products are recyclable except $C_3F_8$ and $C_2F_5Cl$.

Examples on Table I which show good yields to $CF_3$—$CFCl$—$CF_3$ and intermediates which can be recycled are Examples 2–4 and 7.

EXAMPLE 31

This example was carried out in a two-inch by five-foot (5 cm×1.5 m) tubular Inconel ® reactor, giving $CF_3CFClCF_3$ as the chief product. Feed rates in moles/hour were 90 for HF, 35 for $Cl_2$, and 1.5 for propylene. The temperature was 440° C. and the pressure was 115 pounds per square inch (790 kPa). Conversions to various products were:

$C_3F_7Cl$: 75
$C_3F_6Cl_2$: 7
$C_3F_5Cl_3$: 5
$C_3F_7H$: 3
$C_3F_6ClH$: 5
$C_3F_8$: 2
$C_2F_5Cl$: 2

EXAMPLES 32-33

The reactor was a 1 inch (2.54 cm) Inconel® tube packed with 50 inches (1.27 m) of catalyst bed. The catalyst was chromium oxide trihydrate from Shepherd Chemical Company. In this flow system, HF and propylene were mixed and chlorine was added, and the mixture was passed into the reactor. Table IV shows the results obtained, with very good yields to $CF_3$—$CFCl$—$CF_3$ and recyclables.

EXAMPLES 34-41

Several pressure chlorofluorinations were carried out to show that underfluorinated byproducts can be recycled, with or without added propylene. The reactor was an Inconel® tube 2"×5 ft (5.1 cm diameter × 1.52 m), and the catalyst was the same as in Example 29. The pressure was 690 kPa. The "recycle organic" feed was the product of the chlorofluorination of propylene from which the $C_3F_8$ and $CF_3$—$CFCl$—$CF_3$ had been largely removed by distillation, and this feed composition is shown in the first column of Table V. From these experiments it was demonstrated that the byproducts in the chlorofluorination can be recycled to make $C_3F_8$ and $CF_3$—$CFCl$—$CF_3$.

Step Ib) Dehalogenation of $CF_3$—$CFCl$—$CF_3$.

Ib (i) Hydrogenation.

EXAMPLE 42

A 1:1 molar mixture of hydrogen and $CF_3$—$CFCl$—$CF_3$ was passed over a $BaCrO_4$-modified copper chromite catalyst at 400° C. and atmospheric pressure at a contact time of 15-20 seconds. In several experiments, the once-through conversion to hexafluoropropylene was 60-70%, with $C_3F_7H$ the major by-product. This could be recycled to step (a) for further chlorination, so the overall yield was excellent.

EXAMPLES 43-45

For these examples, an Inconel® 600 U-tube reactor was made from 24 inches (61 cm) of 0.5 inch (1.3 cm) tubing. Each arm of the U-tube was 8 inches (20.3 cm) long, as was the bottom. The inlet and outlet to the reactor were ¼ inch (0.64 cm) tubing, and tees allowed ⅛ inch (0.32 cm) thermowells to be placed in each end of the tube. The reactor tube was totally filled with catalyst so that as the cool feed gases were heated, they were in contact with the catalyst. The inlet thermowell indicated that the gases were at reaction temperature within the first 4 inches (10.2 cm) of the reactor length. Because of the preheat length and the length of tubing above the level of the alundum, the actual heated length of the reactor was assumed to be 12 inches (30.5 cm). A separate thermocouple was kept in the fluidized bath to verify the batch temperature.

The cooled product from the reactor was passed into a small polypropylene trap, then into a 20% KOH scrubber made of polypropylene. The heat of reaction of HF and HCl with the alkali was never great enough to heat the solution above 50° C. The product then went through a water scrubber, a small bed of Drierite®, and then to a cold trap in dry ice/acetone where the products and unconverted reactants were collected.

The main analysis tool used for this work was a temperature programmable Hewlett-Packard 5880A gas chromatograph with a thermal conductivity detector. This dual column unit was equipped with a pair of 8-foot × ⅛ inch (2.43 m × 0.32 cm) stainless steel columns packed with 1% SP-1000 on 60/80 mesh Carbopack B purchased from Supelco, Inc (catalog no. 1-2548). These columns were run with helium flows of 30 cc/minute. The column was started at 50° C. for three minutes, then heated to 150° C. at a rate of 20° C./minute, and held there for another 15 minutes if necessary.

Three methods were employed in preparing the various catalysts:

A. Pyrolysis of nitrates. In this method the ingredients such as commercial copper chromite, chromium nitrate, $MoO_3$, etc., were prepyrolyzed in a resin kettle until all the removable water and volatiles were gone, and then the residue was calcined at 650° C. for at least three hours, usually overnight.

B. The various metal cations were precipitated from aqueous solution by adding KOH and KF solutions. The crude solids were filtered, washed well with water, prepyrolyzed and calcined as above.

B*. This method was similar to B, except that precipitation was sequential, rather than simultaneous. Typically, $CaF_2$ was precipitated first, allowed to age at least 24 hours, and only then were the hydrated oxides of transition metals precipitated onto the $CaF_2$ particles.

Several dozen catalysts were evaluated, and most of them gave 80-97% yield from $CF_3$—$CFCl$—$CF_3$ to hexafluoropropylene. Three of the best runs are shown as Examples 43-45.

The catalyst for Example 43 was $CuO/Cr_2O_3/NiO/0.9\ MoO_3/2.1\ CaF_2$, made by method B.

Example 44 used a $CuO/NiO/Cr_2O_3/2.7CaF_2$ catalyst, prepared by method B*, which performed for over 130 hours of intermittent hydrogenation, and was still active as the experiment was voluntarily terminated.

Example 45 used as catalyst $CuO/1.2\ Cr_2O_3/0.9\ NiO/1.7\ CaF_2/K^+$, prepared by method A.

The results for these examples are shown in Table VI.

Example 45A used pellets of a $CuO/NiO/Cr_2O_3/2.7CaF_3$ catalyst which had been soaked in KOH until they contained, after drying, 7.9 weight percent K. The yield to HFP at 400° C. or at 420° C. after extended operation was quite superior to that obtained with similar catalysts containing 0.08% or 0.1.2% K, and was slightly superior to that obtained with similar catalysts containing 4.6, 8.9, 9.6, and 15.1% K.

Any by-products made in the hydrogenation step are recycled to step (a), so they do not represent a yield loss.

EXAMPLE 46A

This hydrogenation was also carried out at elevated pressure, as shown in this Example. A reactor was made of Inconel® tubing with inside diameter 0.19 inches (0.48 cm). The reactor was charged with 1.0 g of $CuO/NiO/Cr_2O_3/2.7CaF_2$, which was conditioned with hydrogen at atmospheric pressure at 550° C. for one hour. Then the reactor was pressurized with nitrogen and fed 95% pure $CF_3$—$CFCl$—$CF_3$ and hydrogen at 150-200 psig (1034-1379 kPa) continuously at 420° C. for 46 hours. The conversion of $CF_3$—$CFCl$—$CF_3$ was 20%, and the yield of hexafluoropropylene from converted $CF_3$—$CFCl$—$CF_3$ was 98-100%.

For comparison, a similar run was made under similar conditions with the $Cu/Ni/Cr_2O_3$ catalyst of U.S. Pat. No. 2,900,423, which gave higher yield to hexafluoropropylene for the first 10 hours, after which the yield decreased sharply while the yield in Example 46 was steady or increased.

Ib (ii). Reaction with a suitable reducing metal.

EXAMPLE 46

This example describes the preparation and testing of $CuO/NiO/Cr_2O_3/2.7$ $CaF_2$ containing various amounts of added K.

Aqueous calcium nitrate (2.7 moles) was mixed with 5.4 moles of aqueous KF, heated and stirred briefly at 100° C. to form a slurry of $CaF_2$. To this slurry were added 1 mole of chromium nitrate, and 1 mole of chromium nitrate as solids. The slurry was stirred at 70°-80° C. until the salts (other than $CaF_2$) dissolved. Then 0.1 mole of aqueous KOH was added over a period of 1 hour and the mixture was boiled briefly. The slurry was cooled to 40°-50° C. and filtered. The solid was washed exhaustively to reduce the K content to an undetectable level. After drying, KOH was added as a solution in quantities sufficient to provide the K contents shown in Table 8. After drying, the catalyst was calcined at 600° C. for 8-16 hours, then granulated and screened to 1-2 mm particles.

Hydrodehalogenation performance was tested in a reactor comprising a 6.4 mm outside diameter U-tube of Inconel ®. In each reaction 1 gram of the catalyst was loaded in the reactor along with 1.5 grams of Inconel ® chips which served as a preheat section. The Inconel ® reactor was immersed in a sand bath for heating purposes. The respective catalysts were reduced by heating at atmospheric pressure in 50 cc/min of $H_2$ at 25°-520° C. and holding at this temperature for 3 hours. The reaction was then conducted at 1700 kPa (250 psig) and 420° C. with a hydrogen feed rate of 22 std. cc/min $H_2$ and a $CF_3CFClCF_3$ feed rate of 11 3 grams/hour (1:1 mol ratio). Performance was measured by taking seven on-stream gas samples at forty-minute intervals, analyzing using a gas chromatograph, and averaging the results.

Next, the catalyst was subjected to a reactivation sequence which comprised a 15 minute nitrogen-gas purge at atmospheric pressure and 420° C., followed by oxidation for one hour in 30 cc/min air at a catalyst-bed inlet temperature of 420° C., a 15 minute nitrogen-gas purge, then reduction using hydrogen at 520° C. for 65 minutes, and cooling the catalyst to 400° C. in a nitrogen atmosphere over a 20 minute period.

Next, synthesis activity at 400° C.–420° C. was again measured using the same reaction conditions as above-described. Seven syntheses samples were taken at regular intervals at 400° C., followed by eight sample sequences taken at regular intervals at 420° C., and then at 400° C.. Four cycles were conducted using catalyst samples containing 0.08 to 15.1 weight percent K. The results are set forth in Table VIII.

Cycles 3 and 4 are reported in Table VIII; the selectivity pattern in the last two cycles of the experiment is a useful predictor of long-term catalyst performance. Selectivity in Table VIII is defined as mols of HFP produced per mol of $CF_3CFClCF_3$ consumed based upon gas chromatography analysis of reaction off-gas. Table VIII shows that the average selectivity of all catalysts with a potassium content of 4.6% or higher was higher in the fourth test cycle than in the third. Catalysts with a potassium content of 1.2% or less show a fall-off in selectivity in the last two cycles.

The catalyst with a potassium content of 7.9 weight percent was tested for 1070 hours and found to be active and selective in the synthesis of hexafluoropropylene from $CF_3CFClCF_3$ at the end of the test.

The above Examples demonstrate that potassium extends the life and enhances the activity of the catalyst.

EXAMPLE 47

Into a one-liter autoclave containing a few steel bearings to facilitate agitation were placed 65 g. zinc dust, 15 g. copper powder, and 250 ml. acetonitrile. The autoclave was cooled and charged with 100 g. of halocarbons, of which 96.3 g. was $CF_3—CFCl—CF_3$, 0.7 g. was hexafluoropropylene, and 1.2 g. was $C_3F_7H$. The autoclave was shaken for 8 hours at 150° C. After cooling to room temperature, the contents were vented slowly into a cylinder cooled to −80° C. Gas chromatographic analysis of the product showed 55% of the $CF_3—CFCl—CF_3$ was converted. The yield to hexafluoropropylene was 29% and the yield to $C_3F_7H$ was 68%. This by-product can be chlorinated to $CF_3—CFCl—CF_3$ for recycle.

II. Sequences of Reactions Based on $CF_3CCl_2—CF_3$

IIA.

a) A feed containing at least one of the class consisting of propane, propylene, and a partially halogenated three-carbon acyclic hydrocarbon is chlorofluorinated to $CF_3—CCl_2—CF_3$. Less highly fluorinated by-products such as $CF_3—CCl=CCl_2$, $CF_3—CCl_2—CF_2Cl$, and $CF_3—CCl_2—CFCl_2$ may be recycled to the chlorofluorination step (a) or fed to the fluorination step (b).

b) $CF_3—CCl_2—CF_3 + HF \rightarrow CF_3—CFCl—CF_3$ c) $CF_3—CFCl—CF_3$ is dehalogenated to hexafluoropropylene

EXAMPLES OF SEQUENCE IIA (EXAMPLES 1-9)

IIA a) for this step (a), chlorofluorination to $CF_3—CCl_2—CF_3$, recycling all more lightly fluorinated intermediates and also $CF_3—CFCl—CF_2Cl$, see the section on Chlorofluorination Experiments, especially Examples 1-6 and 8. Example 9 makes a useful mixture of $CF_3—CCl_2—CF_3$ and $CF_3—CFCl—CF_2Cl$.

EXAMPLE 48

Propylene was chlorofluorinated over $CrF_3.3.5H_2O$ at 440° C. and 115 psia (793 kPa) using a feed of 1.0 mole/hr propylene, 30 moles/hr chlorine, and 30 moles/hr HF. Yields were 12% to $CF_3—CCl_2—CF_3$, 42% to $CF_3—CCl_2—CF_2Cl$, 18% to $CF_3—CCl_2—CFCl_2$, 4% to $C_3F_4Cl_2$, 13% to $C_3F_3Cl_3$, 5% to $C_3F_3HCl_2$, 0.4% to $C_3F_3HCl_4$, and 3% to 2-carbon compounds. This corresponds to a yield to $CF_3—CCl_2—CF_3$ and recyclables of 93.3%.

IIA b)

EXAMPLE 49

$CF_3—CCl_2—CF_3$ (64–403 cc/minute) and HF (50 cc/minute) were passed over $Cr_2O_3$ at 400° C. at a contact time of 18-71 seconds. Analysis showed about 28% conversion of the starting material. The conversion to $CF_3—CFCl—CF_3$ was 26%, corresponding to a yield of 91%. The results were independent of the ratio of HF to $CF_3—CCl_2—CF_3$.

At the end of this experiment, which was on stream about 65 hours, the feed composition was changed by the addition of 10 cc/hour of chlorine. This improved the yield, measured after another 16 hours on stream, to 93-95%, though the conversion of starting material decreased measurably. This confirms the known observation that the overall performance of a catalyst system frequently improves when a small amount of oxidant is added to the feed. While oxygen might be used as the oxidant, chlorine is preferred because it avoids the possibility of adding water to the reaction mixture.

EXAMPLE 50

In this Example, the catalyst was 9 wt. % $CrCl_3$ on Harshaw #3945 $Al_2O_3$, a low alkali aluminum oxide support. It was pretreated with 450 cc/minute HF and 1000 cc/minute dry air at 250°–410° C. for 20 hours. The treated catalyst had an apparent density of 0.984 g/cc. $CF_3$—$CCl_2$—$CF_3$ was then fed at 18 cc/minute, along with 50 cc/minute HF at 450° C. for a contact time of 22.2 seconds. After 40 hours, the conversion to $CF_3$—$CFCl$—$CF_3$ was 33% and recovered reactant was 63%, for a yield of 90%.

EXAMPLES 51-57

Under some conditions a mixture of $CF_3$—$CCl_2$—$CF_3$ and $CF_3$—$CFCl$—$CF_2Cl$ is obtained, and Table VII shows that this mixture can be converted to $CF_3$—$CFCl$—$CF_3$ in moderate conversion and very good yield. These results were obtained in a 14 inch (35.6 cm) by ½ inch (1.27 cm) diameter Inconel® 600 reactor tube with an inside diameter of 0.43 inches (1.1 cm) in a split tube furnace using 34 grams of chromium oxide catalyst at the conditions shown in Table VII. The volume of the tube at temperature was 19 cc. The reactants (feed composition) and products are on an HF and HCl free basis, as these materials were scrubbed from the product stream.

EXAMPLES 58

$CF_3$—$CFCl$—$CF_2Cl$ was reacted with HF over the same chromium oxide catalyst at 450°–470° C. in a ¾ inch (1.9 cm) Inconel® 600 reactor that was 26 inches (66 cm) long, of which 20 inches (51 cm) was at temperature. Typical results for runs using a feed rate of 0.95 moles/hour of $CF_3$—$CFCl$—$CF_2Cl$ and 1.1 moles/hour of HF, expressed in gas chromatograph area %, were:

$CF_4$: 0 1
$C_3F_8$: 2.2
$CF_3$—$CFCl$—$CF_3$: 45.8
$C_2F_5$—$CF_2Cl$: 3.6
$CF_3$—$CCl_2$—$CF_3$: 40.0
$CF_3$—$CFCl$—$CF_2Cl$: 6.0
$CF_3$—$CCl$=$CF_2$: 0.2

Note that the majority of the reactant that was not converted to the desired product was isomerized to the useful $CF_3$—$CCl_2$—$CF_3$. The yield to $CF_3$—$CFCl$—$CF_3$ and recyclable intermediates was 93%.

EXAMPLE 59

$CF_3$—$CCl_2$—$CF_3$ (12 cc/min) and HF (48 cc/min) were passed over $Cr_2O_3$ at 465° C. and a contact time of 7.6 seconds. The conversion to the desired product decreased with time, as usually happens in catalytic reactions, but after 850 hours on stream, the product contained 70% starting material, 26% $CF_3$—$CFCl$—$CF_3$, 0.9% perfluoropropane, 0.1% $C_3F_6HCl$, and 0.1% $CF_3$—$CCl$=$CF_2$. Thus the yield from converted starting material was 87%.

EXAMPLE 60

Similar results were obtained in shorter runs at 100–200 psig (690–1380 kPa) over the same kind of catalyst. For example, at 100 psig (690 kPa), 23 cc/min of $CF_3$—$CCl_2$—$CF_3$ and 53 cc/min HF were passed over $Cr_2O_3$ at a contact time of 24 seconds at 437° C. to give 32% conversion to $CF_3$—$CFCl$—$CF_3$ at high yield after 34 hours on stream.

EXAMPLE 61

This step (b) reaction was also carried out at a pressure of 100 psig (690 kPa). The reaction was carried out in a U-tube with inside diameter 0.43 inches (1.1 cm), using 30 cc $Cr_2O_3$ catalyst at 400°–437° C. The flow of HF was 53 cc/minute and the flow of $CF_3$—$CCl_2$—$CF_3$ was 23 cc/minute. The contact time was 24 seconds. The results are presented below:

| Temp, °C. | Conversion to $CF_3$—$CFCl$—$CF_3$ | Yield (assuming other products were starting material) |
|---|---|---|
| 400 | 5.5% | 89% |
| 412 | 10 | 83 |
| 425 | 20 | 88 |
| 437 | 32 | 86 |

The halogen exchange reaction of step (b) was also carried out under completely different conditions, using $SbF_5$ reactant. In general, replacement of Cl with F can be carried out with Sb fluorides in the (III) or (V) valence state, or a mixture of these. Sb chlorides plus HF can also be used. The temperature range can be 25°–250° C., and the time can be 15 minutes to 15 hours. Preferably, the temperature is 150°–200°, the reagent is $SbF_5$, and the time is long enough to provide a reasonable conversion of starting material. Higher temperature, longer time, and higher Sb valence tend to higher conversion. As pointed out in Sheppard and Sharts, Organic Fluorine Chemistry W. A. Benjamin Inc. 1969 the presence of F on a carbon adjacent to a C—Cl bond deactivates the Cl toward replacement using Sb halide. The group —$CCl_3$ is easier to fluorinate than the group —$CCl_2$—. Carbon-fluorine bonds activated by an adjacent double bond react more readily with Sb fluorides.

EXAMPLE 62

20.6 g $SbF_5$ and 20 g $CF_3$—$CCl_2$—$CF_3$ were charged to a 150 ml Hastelloy pressure tube and agitated for 4 hours at 200° C. The tube was cooled to room temperature and discharged into an Orsat bulb for analysis, which showed 70% $CF_3$—$CFCl$—$CF_3$ and 29% starting material. Thus the conversion was 70% and the yield from converted starting material was 98%.
IIA
c) See step I(b)
IIB.
a) Chlorofluorination of a feed containing at least one of the class consisting of propane, propylene, and a partially halogenated three-carbon acyclic hydrocarbon to a mixture of $CF_3$—$CCl_2$—$CF_3$ and $CF_3$—$CFCl$—$CF_2Cl$, optionally recycling more lightly fluorinated by-products
b) $C_3F_6Cl_2$ is converted to $CF_3$—$CFCl$—$CF_3$ by transhalogenation or by reaction with HF. In the case of disproportionation, by-products can be recycled to step (a)

c) $CF_3-CFCl-CF_3$ is dehalogenated to hexafluoropropylene.

EXAMPLES OF SEQUENCE IIB

IIB
a) For examples of step (a), see the section on chlorofluorination.

IIB b)

EXAMPLE 73

In step (b), transhalogenation or disproportionation, $CF_3-CFCl-CF_2Cl$ (the pure isomer, in this example) (1.67 ml/minute) was passed over 181.2 ml of $Cr_2O_3$ at 420° C. at a contact time of 24 seconds. Conversion to $CF_3-CFCl-CF_3$ was 7% and conversion to $CF_3-CCl_2-CF_3$ was 55.3%, while 6.5% of the starting material was recovered. Some less highly fluorinated by-products were obtained and could be recycled.

Example 22 of U.S. Pat. No. 3,258,500 shows that the reaction of $CF_3-CFCl-CF_2Cl$ with HF over chromium oxide at 425° C. gave 96.7% yield of $CF_3-CFCl-CF_3$ based on recovered organic products. For other examples of the reaction of $C_3F_6Cl_2$ with HF, see IIA (b).

Conditions for the chlorine replacement reaction with antimony fluoride are similar to those described in IIA (b).

IIB c) step (c) is the same as I(b).

IIC.

a) Chlorofluorination of a feed containing at least one of the class consisting of propane, propylene, and a partially halogenated three-carbon acyclic hydrocarbon to a mixture of $C_3F_6Cl_2$ and $C_3F_5Cl_3$ and $C_3F_4Cl_4$, optionally recycling more lightly fluorinated by-products b) Reaction of this mixture with HF to give $CF_3-CFCl-CF_3$, optionally recycling more lightly fluorinated by-products c) Dehalogenation of $CF_3-CFCl-CF_3$ to hexafluoropropylene.

EXAMPLES OF SEQUENCE IIC

IIC
a) As to step (a), Table I contains several examples (5-18) in which there is an excellent yield to a combination of $C_3F_6Cl_2$ and $C_3F_5Cl_3$ and $C_3F_4Cl_4$. Catalysts that gave particularly good total conversions to these three compounds include compounds of Nd, Ce, Y, Fe, Pr, Sm, Rh, or Cr supported on carbon, $CoO/Cr_2O_3$, $NiO/Cr_2O_3$, and $RhCl_3/Cr_2O_3$. These are the catalysts that were run at the preferred contact time and temperature to give the desired results.

IIC
b) The conditions used in IIA(b) are suitable for this step.

IIC
c) For step (c), see I(b)

III. Sequence of Reactions based on $CF_3-CCl_2-CF_2Cl$ a) Chlorofluorination of a feed containing at least one of the class consisting of propane, propylene, and a partially halogenated three-carbon acyclic hydrocarbon to $CF_3-CCl_2-CF_2Cl$, optionally recycling more lightly fluorinated by-products b) $CF_3-CCl_2-CF_2Cl+HF \rightarrow CF_3-CFCl-CF_3$, optionally recycling $CF_3-CCl_2-CF_3$ c) Dehalogenation of $CF_3-CFCl-CF_3$ to hexafluoropropylene.

EXAMPLES OF SEQUENCE III a) For this step (a), see the section on chlorofluorination, especially Examples 6, 18, and 21. See also Example 48 under IIA (a) which gave 42% conversion to $CF_3-CCl_2-CF_2Cl$ at a yield to this product plus recyclable intermediates of 82%, 12% of the yield loss being to $CF_3-CCl_2-CF_3$, a useful product in other sequences of reaction steps.

b) For this step (b), chlorofluorination of $CF_3-CCl_2-CF_2Cl$ results in the formation of $CF_3-CFCl-CF_3$, and simple reaction with HF is equally effective, since the starting material already contains more than enough chlorine. $CF_3-CCl_2CF_3$ is also obtained. See IIA(b) for the conversion of $CF_3-CCl_2-CF_3$ to $CF_3-CFCl-CF_3$.

FIG. 3., using $Cr_2O_3$ catalyst, shows that at 350°-500° C., chlorofluorination of propylene gives increasing amounts of $CF_3-CFCl-CF_3$ and substantially no $CF_3-CCl_2-CF_2Cl$. This means that contacting $CF_3-CCl_2-CF_2Cl$ with HF at 350°-500° C. over this catalyst will give good conversions to $CF_3-CFCl-CF_3$, along with substantial amounts of $CF_3-CCl_2-CF_3$, which can be recycled. See also the conditions used in IIA(b) for reaction with HF or Sb fluoride.

c) step III(c) is the same as I(b).

IV. Sequence Based on $CF_3-CCl_2-CFCl_2$ a) Chlorofluorination of a feed containing at least one of the class consisting of propane, propylene, and a partially halogenated three-carbon acyclic hydrocarbon to $CF_3-CCl_2-CFCl_2$ b) $CF_3-CCl_2-CFCl_2+HF \rightarrow CF_3-CFCl-CF_3$ c) Dehalogenation of $CF_3-CFCl-CF_3$ to hexafluoropropylene a)

EXAMPLE 75

In an example of Step a), propylene was chlorofluorinated over a catalyst of $CaCl_2$ and $CoCl_2$ on carbon at 400° C. and a contact time of 6 seconds. The flow of propylene was 3.3 ml/minute, that of HF was 58 ml/minute, and that of chlorine was 29 ml/minute. The product was 24% $CF_3-CCl_2-CFCl_2$, 68% $CF_3-CCl=CCl_2$, 2% $C_2F_5Cl$, and 4% H-containing three-carbon halocarbons, which can be recycled. Thus the yield to $CF_3-CCl_2-CFCl_2$ plus recyclable by-products was 96%.

EXAMPLES 76-80

See Table I.

b) As to step (b), chlorofluorination of $CF_3-CCl_2-CF_2Cl$ results in the formation of $CF_3-CFCl-CF_3$, and simple reaction with HF is equally effective, since the starting material already contains more than enough chlorine. $CF_3-CCl_2-CFCl_2$ can be similarly converted to $CF_3-CFCl-CF_3$.

FIG. 3, using $Cr_2O_3$ catalyst, shows that at 350°-500° C., chlorofluorination of propylene gives increasing amounts of $CF_3-CFCl-CF_3$ and substantially no $CF_3—CCl_2—CFCl_2$. This means that contacting $CF_3—CCl_2—CFCl_2$ with HF at 350°–500° C. over this catalyst will give good conversions to $CF_3—CF$-Cl—$CF_3$, along with substantial amounts of $CF_3—CC$-

$l_2—CF_3$, which can be recycled. See also the conditions for IIA(b) for the reaction with HF or Sb fluorides.

c) For step (c) see I(b)

TABLE I

CHLOROFLUORINATION OF PROPYLENE - PREDOMINANT PRODUCTS $CF_3CCl_2CClF_2$, $CF_3CCl_2CF_3$ AND $CF_3CFClCClF_2$

| EXAMPLE | CATALYST | TEMP. | CT | HF | $Cl_2$ | $C_3H_6$ | CONV TO $C_3F_5Cl_3$ | YIELD TO $C_3F_5Cl + R$ | CONV TO $C_3F_6Cl_2$ | YIELD TO $C_3F_6Cl_2 + R$ |
|---|---|---|---|---|---|---|---|---|---|---|
| 1 | $CoO/Cr_2O_3$ (20 g) | 460° | 0.12 | 65 | 32 | 2 | | | 58% | 92% |
| 2 | Cr.oxide (25 g) | 445° | 0.04 | 235 | 105 | 5 | | | | |
| 3 | Cr.oxide on alumina (25 g) | 445° | 0.22 | 43 | 25 | 1 | | | 67% | |
| 4 | $Cr_{.5}Mn_{.5}O_2$ (25 g) | 400° | 0.03 | 370 | 200 | 10 | | | 62% | |
| 5 | $NdCl_3$/C (10 g) | 440° | 6.0 | 49 | 24 | 3 | | | 65% | 90% |
| 6 | $FeCl_3$/C (10 g) | 400° | 6.0 | 53 | 27 | 3 | | | 62% | 97% |
| 7 | $Cr_2O_3$ (10 g) | 400° | 6.0 | 50 | 26 | 3 | | | 67% | |
| 8 | $CrCl_3$/C (0.1X) | 400° | 20 | 50 | 25 | 3 | | | 69% | 91% |
| 9 | $RhCl_3/Cr_2O_3$ (15 g) | 310° | 0.17 | 50 | 24 | 3 | | | 30% | 88% |
| 10 | $CeCl_3$/C (10 g) | 400° | 6.0 | 52 | 26 | 3 | | | 36% | 87% |
| 11 | $YCl_3$/C (10 g) | 400° | 6.0 | 50 | 26 | 3 | | | 35% | 88% |
| 12 | $PrCl_3$/C (10 g) | 400° | 6.0 | 52 | 27 | 3 | | | 12% | 96% |
| 13 | $SmCl_3$/C (10 g) | 400° | 8.0 | 52 | 25 | 3 | | | 21% | 90% |
| 14 | $RhCl_3$/C (8 g) | 450° | 0.06 | 50 | 25 | 3 | | | 47% | 86% |
| 15 | $NiO/Cr_2O_3$ (20 g) | 430° | 0.14 | 61 | 31 | 2 | | | 51% | 93% |
| 16 | $La_{.8}Ce_{.2}CrO_3$ (18 g) | 410° | 0.05 | 122 | 87 | 10 | | | 40% | 96% |
| 17 | $La_{.7}Sr_{.3}Cr_{02.7}F_{.6}$ | 370° | | 50 | 27 | 3 | | | 3% | 92% |
| 18 | $CrCl_3$/C (1X) | 400° | 12 | 50 | 25 | 3 | 71% | 83% | 7% | 90% |
| 19 | Cr.oxide/$AlF_3$ (15 g) | 450° | 0.03 | 170 | 105 | 5 | 66% | 95% | | |
| 20 | $Zr_{.5}Cr_{.5}O_{1.5-2.0}$ (10 g) | 490° | 0.06 | 60 | 30 | 2 | | | | |
| 21 | $(ZnCl_2 + CoCl_2)$/C (10 g) | 370° | 0.02 | 250 | 160 | 10 | 91% | 96% | | |
| 22 | $Cr(OH)_3$ (25 g) | 445° | | 60 | 30 | 1 | | | | |
| 76 | $LaCl_3$/C (10 g) | 200° | 5.0 | 103 | 24 | 3 | | | | |
| 77 | $ZnCl_2$/ (10 g) | 445° | 0.07 | 50 | 30 | 3 | | | | |
| 78 | $(CuCl_2 + CoCl_2)$/C (10 g) | 400° | 6.0 | 51 | 25 | 3 | | | | |
| 79 | $(KCl + CoCl_2)$/C (10 g) | 400° | 6.0 | 55 | 26 | 3 | | | | |
| 80 | $(LaCl_3 + CoCl_2)$/C (10 g) | 400° | 6.0 | 51 | 25 | 3 | | | | |

| EXAMPLE | CONV TO $C_3F_7Cl$ | YIELD TO $C_3F_7Cl + R$ | CONV TO $C_3F_8$ | YIELD TO $C_3F_8 + R$ | YIELD TO $C_3F_6Cl_2 + C_3F_7Cl + R$ | CONV TO $C_3F_4Cl_4 + C_3F_5Cl_3 + C_3F_6Cl_2$ | CONV TO $C_3F_4Cl_4$ | YIELD TO $C_3F_4Cl_4 + R$ |
|---|---|---|---|---|---|---|---|---|
| 1 | | 95% | | | | 86% | | |
| 2 | 18% | 71% | 16% | 100% | | | | |
| 3 | 14% | 85% | 7% | 100% | 85% | | | |
| 4 | 11% | 89% | 6% | 100% | | | | |
| 5 | | 90% | | | | 68% | | |
| 6 | | 97% | | | | 82% | | |
| 7 | 17% | 92% | 5% | 97% | 93% | 71% | | |
| 8 | | | | | | 91% | | |
| 9 | | 90% | | | | 87% | | |
| 10 | | 87% | | | | 70% | | |
| 11 | | 88% | | | | 83% | | |
| 12 | | 96% | | | | 71% | | |
| 13 | | 90% | | | | | | |
| 14 | | 86% | | | | 86% | | |
| 15 | | 95% | | | | 86% | | |
| 16 | | 100% | | | 100% | 51% | | |
| 17 | | | | | | 32% | | |
| 18 | | | | | | 90% | | |
| 19 | | 99% | | | | | | |
| 20 | 2% | 78% | 3% | 82% | | | | |
| 21 | | 96% | | | | | | |
| 22 | | | 30% | 100% | | | | |
| 76 | | | | | | | 4% | 100% |
| 77 | | 100% | | | | | 32% | 85% |
| 78 | | | | | | | 31% | 96% |
| 79 | | | | | | | 5% | 95% |
| 80 | | | | | | | 15% | 86% |

The CT or contact time is in seconds and is defined as the ratio of the volume of catalyst (cc) to the total flow of gases (cc/seconds).
The figures for HF, $Cl_2$ and $C_3H_6$ are the flow rates for the individual gases and are expressed in cc/minute.
The figures for $C_3F_4Cl_4$, $C_3F_5Cl_3$, $C_3F_6Cl_2$, and $C_3F_7Cl$ are the yields obtained via a one time pass over the catalyst and the remainder of the products are intermediates which can be recycled to produce additional product.
R = recyclable intermediates.

TABLE II

CHLOROFLUORINATION OF PROPYLENE - CATALYTIC ACTIVITY RELATIVE TO CARBON PELLETS

| EXAMPLE | CATALYST | TEMP. | CT | HF | $Cl_2$ | $C_3H_6$ | CONV TO $C_3F_6Cl_2$ | YIELD TO $C_3F_6Cl_2 + R$ | CONV TO $C_3F_7Cl$ | YIELD TO $C_3F_7Cl + R$ |
|---|---|---|---|---|---|---|---|---|---|---|
| 5 | $NdCl_3$/C (10 g) | 440° | 6.0 | 49 | 24 | 3 | 65% | 90% | | 90% |
| 6 | $FeCl_3$/C (10 g) | 400° | 6.0 | 53 | 27 | 3 | 62% | 97% | | 97% |

TABLE II-continued

CHLOROFLUORINATION OF PROPYLENE - CATALYTIC ACTIVITY RELATIVE TO CARBON PELLETS

| EXAMPLE | CATALYST | TEMP. | CT | HF | $Cl_2$ | $C_3H_6$ | CONV TO $C_3F_6Cl_2$ | YIELD TO $C_3F_6Cl_2$ + R | CONV TO $C_3F_7Cl$ | YIELD TO $C_3F_7Cl$ + R |
|---|---|---|---|---|---|---|---|---|---|---|
| 7 | $Cr_2O_3$ (10 g) | 400° | 6.0 | 50 | 26 | 3 | 67% | | 17% | 92% |
| 10 | $CeCl_3$/C (10 g) | 400° | 6.0 | 52 | 26 | 3 | 36% | 87% | | 87% |
| 11 | $YCl_3$/C (10 g) | 400° | 6.0 | 50 | 26 | 3 | 35% | 88% | | 88% |
| 12 | $PrCl_3$/C (10 g) | 400° | 6.0 | 52 | 27 | 3 | 12% | 96% | | 96% |
| 13 | $SmCl_3$/C (10 g) | 400° | 8.0 | 52 | 25 | 3 | 21% | 90% | | 90% |
| COMP. 23 | C-pellets (10 g) | 400° | 6.0 | 53 | 26 | 3 | 17% | 55% | | |

The CT or contact time is in seconds and is defined as the ratio of the volume of catalyst (cc) to the total flow of gases (cc/seconds).
The figures for HF, $Cl_2$ and $C_3H_6$ are the flow rates for the individual gases and are expressed in cc/minute.
The figures for $C_3F_6Cl_2$, $C_3F_7Cl$ are the yields obtained via a one time pass over the catalyst and the remainder of the products are intermediates which can be recycled to produce additional product.
R = recyclable intermediates.

TABLE III

CHLOROFLUORINATION OF PROPANE -
PREDOMINANT PRODUCTS $CF_3CCl_2CF_3$ AND $CF_3CCl_2CF_2Cl$

| EXAMPLE | CATALYST | TEMP. | CT | HF | $Cl_2$ | $C_3H_8$ | CONV TO $CF_3CCl_2CF_3$ | YIELD TO $CF_3CCl_2CF_3$ + R |
|---|---|---|---|---|---|---|---|---|
| 24 | $CrCl_3$/C | 420° | 20 | 93 | 36 | 3.3 | 45% | 86% |
| 25 | $CrCl_3$/C | 420° | 29 | 64 | 24 | 2 | 60% | 89% |
| 26 | $CrCl_3$/C | 420° | 39 | 48 | 18 | 1.5 | 68% | 88% |
| 27 | $CrCl_3$/C | 420° | 59 | 32 | 12 | 1 | 71% | 87% |
| 28 | $CrCl_3$/C | 420° | 117 | 16 | 6 | 0.5 | 81% | 85% |

The CT or contact time is in seconds and is defined as the ratio of the catalyst (cc) to the total flow of gases (cc/seconds).
The figures for HF, $Cl_2$ and propane are the flow rates for the individual gases and are expressed in cc/minute.
Recyclable intermediates excludes $C_3F_7Cl$, $C_3F_8$, $C_3F_6Cl_2$ isomers other than $CF_3CCl_2CF_3$, $CF_3CF_2Cl$, and $C_3F_5Cl_3$ isomers other than $CF_3CCl_2CF_2Cl$.
R = recyclable intermediates.

TABLE IV

| EXAMPLE | 32 | 33 |
|---|---|---|
| Temperature, °C. | 400 | 400 |
| $C_3H_6/Cl_2$/HF | 1/9/25 | 1/7/49 |
| Moles/hour | 7 | 6 |
| Contact time, sec | 15 | 18 |
| $C_3F_8$ | 3% | 4% |
| $CF_3CFClCF_3$ | 19 | 20 |
| $CF_3CCl_2CF_3$ | 53 | 52 |
| $CF_3CCl_2CF_2Cl$ | 7 | 2 |
| $CF_3CF_2CHF_2$ | 2 | 10 |
| $CF_3CFClCHF_2$ | 2 | 4 |
| $CF_3CCl_2CHF_2$ | 8 | 3 |
| $C_{1-2}$ Products | 1 | 4 |
| Conv to $C_3F_8$ | 3 | 3 |
| Conv to $CF_3CFClCF_3$ | 19 | 17 |
| Conv to $CF_3CCl_2CF_3$ | 53 | 45 |
| Yield to $C_3F_8$ + R | 94 | 98 |
| Yield to $CF_3CFClCF_3$ + R | 91 | 94 |

R = Recyclables

TABLE VI

| CONVERSION OF $C_3F_7Cl$ TO $C_3F_6$ | | | |
|---|---|---|---|
| EXAMPLE | 43 | 44 | 45 |
| Temperature, °C. | 399 | 400 | 402 |
| Hours after startup | 1.0 | 1.0 | 3.5 |
| Feed | | | |
| $CF_3CFClCF_3$ | 90% | 77% | 79% |
| $C_2F_5CF_2Cl$ | 7% | 21% | 17% |
| $CF_3CCl=CF_2$ | 2% | 0.9% | 0.7% |
| Product, excluding recovered reactant | | | |
| $C_3F_6$ | 27% | 45% | 49% |
| $C_2F_5-CF_2H$ | 0.5% | 0.6% | 0.6% |
| $CF_3-CFH-CF_3$ | 1% | 0.8% | 0.9% |
| Conversion of $CF_3-CFCl-CF_3$ | 31% | 60% | 63% |
| Yield from $CF_3CFClCF_3$ to $CF_3CF=CF_2$ | 96% | 98% | 97% |
| Contact time, seconds | 11 | 11 | 10 |

TABLE V

CHLOROFLUORINATION OF "RECYCLE" CRUDE

| EXAMPLE | "RECYCLE" ORGANICS | 34 | 35 | 36 | 37 | 38 | 39 | 40 | 41 |
|---|---|---|---|---|---|---|---|---|---|
| Temperature, °C. | | 420 | 450 | 420 | 420 | 420 | 450 | 450 | 450 |
| Feed Rates, mol/hr. | | | | | | | | | |
| $C_3H_6$ | | 0 | 0 | 0.7 | 0 | 0.4 | 0 | 0 | 0.9 |
| "Recycle" | | 1.5 | 5.7 | 2.9 | 3.3 | 1.8 | 3.7 | 11 | 7.6 |
| $Cl_2$ | | 9 | 9 | 29 | 23 | 21 | 23 | 11.5 | 11 |
| HF | | 31 | 36 | 45 | 50 | 41 | 50 | 22 | 22 |
| Products (GC, %) | | | | | | | | | |
| $C_3F_8$ | 0.1 | 2 | 5 | 0.2 | 0.4 | 0.2 | 2 | 4 | 5 |
| $C_3F_7Cl$ | 2 | 17 | 22 | 11 | 11 | 13 | 19 | 22 | 19 |
| $C_3F_6Cl_2$ | 63 | 79 | 70 | 82 | 82 | 82 | 76 | 71 | 72 |
| $C_3F_5Cl_3$ | 12 | 1 | 0.8 | 2 | 3 | 3 | 0.9 | 1 | 2 |
| $C_3F_6HCl$ | 11 | 0.3 | 0.2 | 3 | 1 | 0.9 | 1 | 0.3 | 0.3 |
| Unknowns | 8 | 1 | 2 | 2 | 2 | 0.9 | 1 | 1 | 2 |

TABLE VII

CONVERSION OF $C_3F_6Cl_2$ TO $C_3F_7Cl$

| EXAMPLE | FEED | 51 | 52 | 53 | 54 | 55 | 56 | 57 |
|---|---|---|---|---|---|---|---|---|
| Temperature, °C. | | 422 | 422 | 451 | 424 | 426 | 425 | 427 |
| Gram-mol/hr. | | | | | | | | |
| HF | | 0.25 | 0.25 | 0.25 | 0.5 | 0.5 | 0.75 | 0.75 |
| $C_3F_6Cl_2$ | | 0.25 | 0.25 | 0.25 | 0.25 | 0.25 | 0.25 | 0.25 |
| Contact time, seconds | | 3.1 | 3.1 | 3.1 | 4.7 | 4.7 | 6.2 | 6.2 |
| Gas Composition, % | | | | | | | | |
| $CF_3$—CFCl—$CF_3$ | 0.94 | 41 | 41 | 44 | 49 | 50 | 48 | 45 |
| $C_2F_5$—$CF_2Cl$ | 0.06 | 3 | 3 | 3.9 | 2 | 1 | 1 | 0.7 |
| $CF_3$—$CCl_2$—$CF_3$ | 59 | 45 | 44 | 43 | 25 | 28 | 27 | 19 |
| $CF_3$—CFCl—$CF_2Cl$ | 38 | 8 | 9 | 5 | 20 | 19 | 22 | 34 |
| $C_2F_5CFCl_2$ | | 0.4 | 0.1 | 0.1 | 0.1 | 0.1 | 0.1 | 0.1 |
| $C_3F_8$ | | 1 | 0.9 | 2 | 2 | 0.4 | 0.4 | 0.3 |
| $CF_4$ | | 0 | 0 | 0 | 0.7 | 0 | 0 | 0.005 |
| Miscellaneous | 2.5 | 2 | 3 | 2 | 2 | 0.8 | 0.9 | 1 |
| Conversion of $C_3F_6Cl_2$, % | | 44 | 44 | 49 | 51 | 50 | 47 | 44 |
| Yield to $CF_3$—CFCl—$CF_3$, % | | 94 | 93 | 91 | 96 | 102 | 102 | 103 |

TABLE VIII

EFFECT OF POTASSIUM CONTENT ON CATALYST PERFORMANCE

| Example | W % K | Sel. to HFP[1] at 420° C. (Cycle 3) | Sel. to HFP at 400° C. (Cycle 4) |
|---|---|---|---|
| a | 1390 | 74.8 | 82. |
| b | 9.60 | 77.5 | 83. |
| c | 8.90 | 74.2 | 76.1 |
| d | 7.9 | 78.5 | 822 |
| e | 4.60 | 717, | 74.7 |
| f | 3.0 | 719, | 46.6 |
| g | 0.08 | 45. | 20.6 |

[1]Sel. to HFP = Selectivity to Hexafluoropropylene

We claim:

1. A process for the preparation of hexafluoropropylene comprising, under effective reaction conditions:
   (a) chlorofluorinating a member of the group consisting of propane, propylene and partially halogenated C-3 acyclic hydrocarbons, by contacting with hydrogen fluoride and chlorine in a hydrogen fluoride/chlorine ratio of about from 1 to 7 in the presence of a solid metal-containing catalyst, to produce saturated perhalogenated C-3 chlorofluorocarbons;
   (b) hydrofluorinating any chlorofluorocarbons of (a) that are not $CF_3CFClCF_3$ to produce $CF_3CFClCF_3$ by contacting with hydrogen fluoride in the presence of a catalyst; and
   (c) hydrodehalogenating said $CF_3CFClCF_3$ to hexafluoropropylene in the presence of hydrogen and a catalyst.

2. A process of claim 1 wherein step (a) is carried out in the vapor phase.

3. A process of claim 1 wherein step (c) is carried out in the presence of a K-containing catalyst.

4. A process of claim 1 wherein the catalyst used in step (c) comprises about 1.0 mole CuO/0.2-1 mole NiO/1-3. mole $Cr_2O_3$/4.-21 mole $CaF_2$ further containing 1-20 weight percent of a member of the group consisting of K, Cs and Rb.

5. A process of claim 1 wherein the catalyst used in step (c) comprises about 1.0 mole CuO/0.2-1 mole NiO/1-2 moles $Cr_2O_3$/0.4-1 mole $MoO_3$/0.8-4 moles $CaF_2$ further containing 1-20 weight percent of a member of the group consisting of K, Cs and Rb.

6. A process of claim 4 in which the member of the group in the catalyst is K present in 2-15 weight percent.

* * * * *